(12) United States Patent
Deboeuf et al.

(10) Patent No.: US 10,695,533 B2
(45) Date of Patent: Jun. 30, 2020

(54) ROBOTIC METHOD FOR DRIVING A CATHETER AND A CATHETER GUIDE

(71) Applicant: ROBOCATH, Rouen (FR)

(72) Inventors: Sebastien Deboeuf, Sotteville-les-Rouen (FR); Fabien Destrebecq, Bourgtheroulde (FR); Bruno Fournier, Saint Ouen (FR); Philippe Bencteux, St Martin du Vivier (FR)

(73) Assignee: ROBOCATH, Rouen (FR)

( * ) Notice: Subject to any disclaimer, the term of this patent is extended or adjusted under 35 U.S.C. 154(b) by 283 days.

(21) Appl. No.: 15/580,700

(22) PCT Filed: Jun. 10, 2016

(86) PCT No.: PCT/FR2016/051399
§ 371 (c)(1),
(2) Date: Dec. 8, 2017

(87) PCT Pub. No.: WO2016/198799
PCT Pub. Date: Dec. 15, 2016

(65) Prior Publication Data
US 2018/0185616 A1 Jul. 5, 2018

(30) Foreign Application Priority Data

Jun. 12, 2015 (FR) ..................................... 15 55365

(51) Int. Cl.
*A61M 25/01* (2006.01)
*A61B 34/30* (2016.01)
*A61B 6/12* (2006.01)

(52) U.S. Cl.
CPC ......... *A61M 25/0113* (2013.01); *A61B 34/30* (2016.02); *A61B 6/12* (2013.01); *A61B 2034/301* (2016.02)

(58) Field of Classification Search
CPC ........... A61B 34/30; A61B 8/12; A61B 34/20; A61B 17/320758; A61B 34/35;
(Continued)

(56) References Cited

U.S. PATENT DOCUMENTS 5,116,350 A * 5/1992 Stevens .......... A61B 17/320758
606/159
7,927,310 B2 4/2011 Bencteux et al.
(Continued)

FOREIGN PATENT DOCUMENTS

EP 2 875 792 A1 5/2015
WO 2014/062890 A1 4/2014

OTHER PUBLICATIONS

International Search Report, dated Sep. 22, 2016, from corresponding PCT/FR2016/051399 application.

*Primary Examiner* — Manuel A Mendez
(74) *Attorney, Agent, or Firm* — Young & Thompson (57) ABSTRACT

Disclosed is a robotic method for driving a catheter and a catheter guide, controlling a group of driving members and including: —a first operating mode in which the group of driving members moves the guide forward in translation; a second operating mode in which the group of driving members turns the guide about itself, the method also including a third operating mode in which the group of driving members simultaneously moves the guide forward in translation and turns the guide about itself, alternating between one direction and another.

21 Claims, 5 Drawing Sheets

(58) Field of Classification Search
CPC .............. A61B 19/2203; A61B 34/70; A61M 25/0147; A61M 25/0113; A61M 25/0105; A61M 25/09041; A61M 25/0136
See application file for complete search history.

(56) References Cited

U.S. PATENT DOCUMENTS

| | | |
|---|---|---|
| 2008/0140101 A1* | 6/2008 | Carley ........... A61B 17/320758 606/159 |
| 2010/0204613 A1* | 8/2010 | Rollins ........... A61M 25/09041 600/585 |
| 2013/0035537 A1 | 2/2013 | Wallace et al. |
| 2014/0276389 A1 | 9/2014 | Walker |
| 2014/0277333 A1* | 9/2014 | Lewis ................ A61M 25/0113 623/1.11 |
| 2014/0277334 A1 | 9/2014 | Yu et al. |

* cited by examiner

ROBOTIC METHOD FOR DRIVING A CATHETER AND A CATHETER GUIDE

The present invention relates to robotic methods for driving catheter and catheter guide.

The manual insertion of a catheter and/or a guide in a patient is a relatively conventional surgical procedure. However, since this procedure is monitored by x-rays, the surgeon in charge of this procedure is subject to significant irradiation if the surgeon does such an operation on many patients.

In order to reduce the risks for the surgeon, it is attempted to make such an insertion robotic. Making it robotic is complex because it is difficult to grasp the catheter. The catheter is in fact bathed in storage liquid and must remain sterile. The reliability of these robotic systems is a decisive criterion.

Recently, the U.S. Pat. No. 7,927,310 proposed a driving system managing both the translation and rotation of the catheter. The catheter is kept on a plate rotating relative to a base for driving in rotation. The plate itself comprises a mechanism for driving in translation. Additionally, remote motors, remaining on the frame, and systems for transfer of the movement to the catheter are called on. In fact, it is preferable to not have onboard motors, for reasons of power supply, bulk and sterility.

This configuration therefore proposes a first mode of operation in which the catheter and the catheter guide are going to be able to be advanced in translation.

This configuration therefore also proposes a second mode of operation in which the catheter and the catheter guide are going to be able to turn on themselves in a same direction, the direction of rotation selectable either in clockwise or counterclockwise direction.

However, in some passages through the human circulatory system, like for example a branching of veins or arteries, or for example a lesion, the passage of the catheter and most especially the passage of the catheter guide which precedes it are going to be difficult and risk running up against a blood vessel wall or even catching on and damaging a blood vessel wall or else take a wrong blood vessel near the branching.

To overcome this difficulty, the invention proposes the addition of a third mode of operation in which a slow translation is combined with a rapid alternating rotation of the catheter guide to allow it to pass the sensitive area without hindrance. This slow translation combined with a rapid alternating rotation can be done with the guide alone, the catheter alone, and with the guide and catheter. Even if the guide and catheter are driven, it is possible to apply this third mode of operation only to the guide or to the catheter.

For this purpose, according to the invention a robotic method is provided for driving a catheter or guide, or else catheter and guide, piloting an assembly of drive members and comprising:
- A first mode of operation in which the assembly of drive members advances the guide and/or the catheter in translation;
- A second mode of operation in which the assembly of drive members turns the guide and/or the catheter around itself;
characterized in that the method also comprises:
- A third mode of operation in which the assembly of drive members simultaneously advances the guide and/or the catheter in translation and turns the guide and/or the catheter around itself alternately in one direction and then in the other direction.

For this purpose, according to the invention, a robotic module is also provided for driving catheter or guide, or even catheter and guide, comprising an assembly of drive members that are structured and arranged so as to be able to be piloted in a way to perform the method according to any one of the preceding claims.

For this purpose, according to the invention, a robotic module is again provided for driving catheter or guide, or even catheter and guide, comprising an assembly of drive members that are structured and arranged so as to be able to be piloted:
- In a first mode of operation, so as to advance the guide and/or catheter in translation;
- In a second mode of operation, so as to turn the guide and/or the catheter around itself;
Characterized in that the assembly of drive members is also structured and arranged so as to be able to be piloted:
- In a third mode of operation, so as to simultaneously advance the guide and/or the catheter in translation while also turning it around itself alternately in one direction and then in the other.

In preferred embodiments of the invention, use could further be made of one and/or the other of the following arrangements:

Preferably, in the third mode of operation, the assembly of drive members simultaneously advances the guide and/or the catheter in translation according to the variations of the command from a human machine interface and turns the guide and/or the catheter automatically around itself alternately in one direction and then in the other direction. Thus the ergonomics for the practitioner is improved while providing good effectiveness of progression of the catheter guide, and does so without danger for the patient of catching the blood vessel wall.

Preferably, in the third mode of operation, the assembly of drive members simultaneously advances the guide and/or the catheter in translation according to the variations of the command from a human machine interface and automatically turns the guide and/or the catheter around itself alternately in one direction and then in the other direction, where the frequency of alternating rotation is proportional to the speed of translation.

In a first preferred embodiment, for which the practitioner keeps a maximal freedom, a robotic method of driving catheter or guide, or even catheter and guide, is provided for piloting an assembly of drive members and comprising:
- A first mode of operation in which the assembly of drive members advances the guide and/or the catheter in translation depending on variations of the command from a human machine interface;
- A second mode of operation in which the assembly of drive members turns the guide and/or the catheter around itself depending on variations of the command from a human machine interface;
characterized in that the method also comprises:
- A third mode of operation in which the assembly of drive members simultaneously advances the guide and/or the catheter in translation and turns the guide and/or the catheter around itself alternately in one direction and then in the other direction, depending on variations of the command from a human machine interface.

In a second preferred embodiment, for which the practitioner keeps an optimized ease of use, a robotic method of driving catheter or guide, or even catheter and guide, is provided for piloting an assembly of drive members and comprising:

A first mode of operation in which the assembly of drive members automatically advances the guide and/or the catheter in translation;

A second mode of operation in which the assembly of drive members automatically turns the guide and/or the catheter around itself;

characterized in that the method also comprises:

A third mode of operation in which the assembly of drive members automatically and simultaneously advances the guide and/or the catheter in translation and turns the guide and/or the catheter around itself alternately in one direction and then in the other direction.

Preferably, in the third mode of operation, the assembly of drive members simultaneously advances the guide and/or the catheter in translation and turns the guide and/or the catheter around itself alternately in one direction and then in the other direction, where the ratio between the frequency of alternating rotation and the speed of translation is adjustable by the user of the method. In this way, according to the intent and skill of the user, the ratio between the frequency of alternating rotation and the speed of translation can be adapted while also possibly allowing the user to advance according to the difficulties encountered at their own pace that this user is going to find useful.

Preferably, in the third mode of operation, the advance in translation of the guide and/or catheter is slower than in the first mode of operation, whereas the alternating rotation of the guide and/or catheter around itself is faster than the rotation of the guide and/or of catheter around itself in the second mode of operation. In that way, the accentuated slowness of the translation coupled with the increased frequency of the alternating rotation makes the passage through sensitive areas more effective, even if it is at the price of an additional expenditure of energy/millimeter traveled by the guide for the catheter.

Preferably, the guide is a wire having a bent-back tip, with the bent-back tip advancing along a direction parallel to the wire while turning around the axis of the wire in the third mode of operation. Thus, the bent-back tip of the wire helps to direct the guide of the catheter in the right direction because of an adequate orientation of this bent-back tip of the wire.

Preferably, the bent-back tip of the guide undergoes at least two changes of direction of rotation in the time that it advances a distance corresponding to the length of the bent-back tip, preferably at least four changes of direction of rotation, still more preferably at least 10 changes of direction of rotation. In that way, the accentuated slowness of the translation coupled with the increased frequency of the alternating rotation makes the passage through sensitive areas more effective, even if it is at the price of an additional expenditure of energy/millimeter traveled by the guide for the catheter.

Preferably, the guide and/or catheter undergoes at least two changes of direction of rotation in the time that it advances a distance corresponding to a length of 5 mm, preferably at least four changes of direction of rotation, still more preferably at least 10 changes of direction of rotation. In that way, the accentuated slowness of the translation coupled with the increased frequency of the alternating rotation makes the passage through sensitive areas more effective, even if it is at the price of an additional expenditure of energy/millimeter traveled by the guide for the catheter.

Preferably, in the third mode of operation, the frequency of changing direction of rotation of the guide and/or catheter is at least 1 Hz, preferably at least 3 Hz, still more preferably at least 10 Hz.

Preferably, in the third mode of operation, the speed of translation of the guide and/or catheter is it most 10 mm/s, preferably at most 3 mm/s, still more preferably at most 1 mm/s.

Preferably, the third mode is used for passing through some areas of branching in the human circulatory system. This third mode of operation is in fact particularly effective for passing through sensitive or difficult areas of the human circulatory system.

Preferably, the third mode is used for passing through some areas of lesions in the human circulatory system. This third mode of operation is in fact particularly effective for passing through sensitive or difficult areas of the human circulatory system.

According to another aspect of the invention, still for helping the guide and/or catheter to pass the sensitive areas, a robotic method of driving catheter or guide, or even catheter and guide, is provided for piloting an assembly of drive members and comprising:

A first mode of operation in which the assembly of drive members advances the guide and/or the catheter in translation;

A second mode of operation in which the assembly of drive members turns the guide and/or the catheter around itself;

characterized in that the method also comprises:

A third mode of operation in which the assembly of drive members simultaneously both advances the guide and/or the catheter in translation and also successively alternates turning the guide and/or catheter around itself always in a single direction followed by stopping this rotation.

Preferably in the third mode of operation, said rotation lasts a shorter time than said stopping.

Preferably in said third mode of operation, said rotation lasts between 0.05 s and 0.2 s, preferably about 0.1 s, said stopping lasts between 0.3 s and 1 s, preferably about 0.5 s, and said translation speed is included between 1 mm/s and 5 mm/s, preferably being about 3 mm/s.

In a sample structural embodiment, it is expected that the assembly of drive members comprise:

A base,

A pair of drive members each having a drive surface, where the pair of drive members can be placed alternately in a drive configuration in which the drive surfaces of the drive members of the pair of drive members are engaged with the guide and/or catheter to be driven and arranged on either side thereof, and in a released configuration in which the drive surface of the drive members of the pair of drive members are not engaged with the guide and/or the catheter;

The pair of drive members is mounted mobile relative to the base along a degree of freedom between a first and second position;

A command member suited for cyclic repeatedly commanding a displacement relative to the base of the drive members of the pair of drive members in drive configuration from the first to the second position, in that way driving the guide and/or catheter relative to the base, and a displacement relative to the base (132) of the drive members from the pair of drive members in released configuration from the second to the first position without driving the guide and/or the catheter relative to the base.

With this embodiment, a simple and effective unwinding of the translation movement is possible.

In a sample structural embodiment, it is also provided that the translation of the drive members relative to the base along a direction transverse to the local longitudinal direction of the guide and/or catheter and in opposite directions is adapted for allowing winding of the guide and/or catheter on drive surfaces around the local longitudinal direction of the guide and/or catheter.

With this embodiment, a simple and effective unwinding of the rotational movement is possible.

In a sample structural embodiment, it is again provided that the base is a first base, the pair of drive members is a first pair of drive members and the robotic module further comprises:

A second base;

A second pair of drive members each having a drive surface, where the second pair of drive members can be placed alternately in a drive configuration in which the drive surfaces of the drive members of the second pair of drive members are engaged with the guide and/or catheter to be driven and arranged on either side thereof, and in a released configuration in which the drive surface of the drive members of the second pair of drive members are not engaged with the guide and/or the catheter;

The second pair of drive members is mounted mobile relative to the second base along a degree of freedom between a first and second position;

The command member is further suited for cyclic repeatedly commanding a displacement relative to the base of the drive members of the second pair of drive members in drive configuration from the first to the second position, in that way driving the guide and/or catheter relative to the second base, and a displacement relative to the second base of the drive members from the second pair of drive members in released configuration from the second to the first position without driving the guide and/or the catheter relative to the second base.

Other features and advantages of the invention will become apparent during the following description of one of the embodiments thereof, given as a nonlimiting example, with reference to the attached drawings.

In the various figures, the same references designate identical or similar items. Unless indicated otherwise, the expressions bent-back end and bend-back tip will be used without distinction for the catheter guide.

Figure 1:
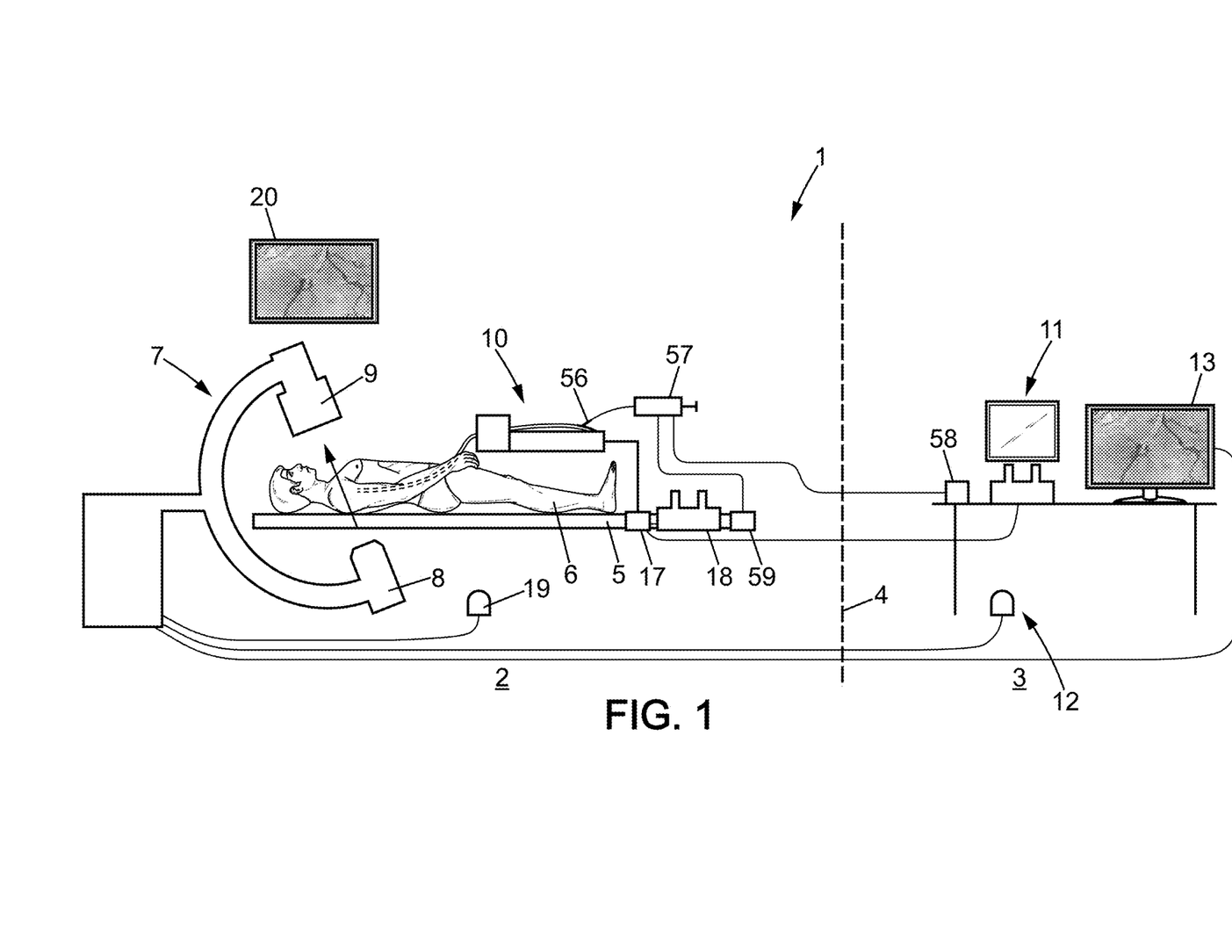
FIG. 1 is a schematic side view of a robotic arteriographic installation.

FIG. 1 schematically shows an arteriographic installation 1. The arteriographic installation 1 is divided into two distinct areas: one operating room 2 and one command room 3. The command room 3 can be close to the operating room 2, separated from it by a simple x-ray blocking wall 4, or remote. The equipment in the operating room 2 and the command room 3 are functionally connected to each other by wire, wireless or network, etc.

The operating room 2 includes an operating table 5 receiving a patient 6. The operating room 2 can also include a medical imager 7 in particular for imaging by x-ray, comprising a source 8 and a detector 9 arranged on either side of the patient, which could be mobile relative to the patient.

The arteriographic installation 1 comprises a robot 10 arranged in the operating room 2.

The arteriographic installation 1 comprises a command station 11 arranged in the command room 3. The command station 11 is suited for remotely commanding the robot 10. The arteriographic installation 1 can also include, arranged in the control room 3, one or more remote controls 12 for the imager 7 communicating with the imager 7 for controlling it from a distance. The arteriographic installation 1 can also include, arranged in the command room 3, a screen 13, communicating with the imager 7, for viewing in real time in the command room 3 the images acquired by the imager 7.

The robot 10 can include a container suited for holding a long flexible medical member 15 to be inserted in a patient's body. The long flexible medical member 15 could for example involve a member to be inserted in a canal of a patient and to be moved in this canal, in particular an artery or vein of the patient, through a catheter introducer providing an access opening into the patient. The long flexible medical member can in particular be a catheter. As a variant, the long flexible medical member can be a catheter guide. A guide generally has a transverse diameter less than that of the catheter, which is generally hollow over a portion close to the patient, even over its entire length, such that the guide can be displaced inside of it, in particular inside the body of the patient. The guide can also comprise a bent-back end, as will be described in more detail below.

The robot 10 may include a drive module for the long flexible medical member 15. The drive module can be commanded from the command station 11 for driving the long flexible medical member relative to the patient along at least one degree of freedom, as will be described in detail subsequently. The drive module may include a communication box 17 providing an interface with the command station 11. As needed, the robot 10 may include a local command box 18, intended to command the robot from the operating room 2 if necessary.

It will additionally be noted that all commands and feedback available in the command room 3 can also be available in the operating room 2 in order for local operation, such as for example a command 19 for the imager and the screen 20 with which to see the images acquired by the imager 7.

The hollow long flexible medical member 15 can be connected to a connector 56 with which to inject a contrast product making the imaging inside the long flexible medical member easier. The arteriographic installation can include a contrast product injector 57 connected to the connector 56 and commanded by a command 58 arranged in the command room 3. A command 59 for the contrast product injector can also be present locally in the operating room 2.

Figure 2A:
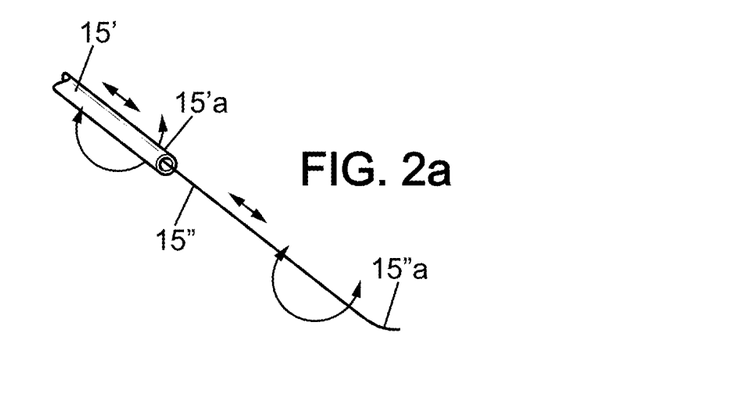
FIGS. 2a-2f are illustrative sketches of modes of displacement of the members to be driven.

FIG. 2a shows the various degrees of freedom conceivable with the present system. The guide 15" can be seen with the front end 15"a thereof slightly curved relative to the main longitudinal axis of the guide and extending out from the front end 15'a of the catheter 15'. The catheter 15' can undergo two distinct motions:

A translation along the longitudinal axis thereof;
A rotation around the longitudinal axis thereof.

These movements can be generated in one direction or the other.

As needed, the catheter 15' can undergo a combined movement of the two simple movements described above.

As needed, the catheter 15' can undergo two combined movements of the two simple movements described above, according to combinations.

What was described above concerning the catheter also applies to the guide.

In some cases, the catheter itself is provided with a curved end, either in order to allow navigation on the same principle as a guide, or to facilitate positioning in an anatomical area having a specific curvature.

Figure 2B:
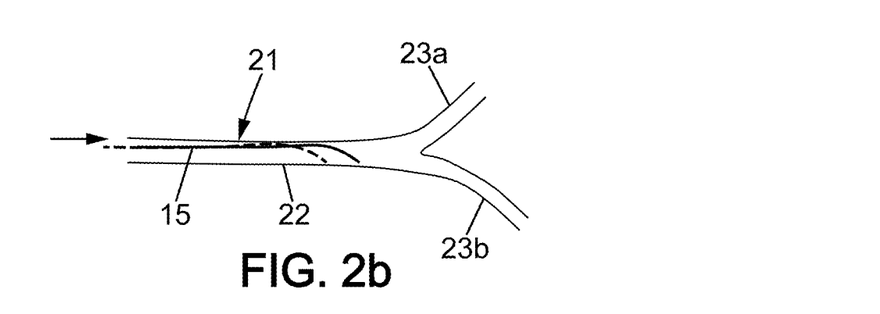

An artery 21 of the patient is shown in FIG. 2b; the artery has a main trunk 22 and two branches 23a, 23b off the main trunk. FIG. 2b shows the displacement of a long flexible medical member 15 (here a guide 15") according to a translation between a back position shown with dashes and a foreword position shown with solid lines. On FIG. 2c, in the same artery, a rotation of the long flexible medical member 15 between a first position, shown with dashes, where the long flexible medical member is ready to undergo a translation towards the branch 23a, and a second position, shown in solid lines, where the long flexible medical member is ready to undergo a translation towards the branch 23b, is shown.

The long flexible medical member can be driven by the drive members according to the one or more displacements described above. The drive members can be arranged in pairs.

Figure 2C:
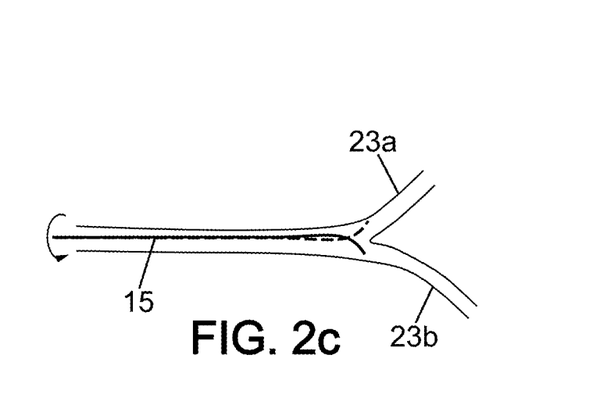

In FIGS. 2a to 2c movements of translation and rotation corresponding to the first and second modes of operation are shown.

Figure 2D:
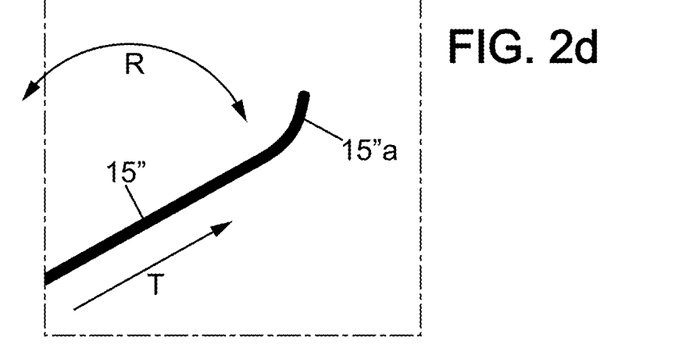
Figure 2E:
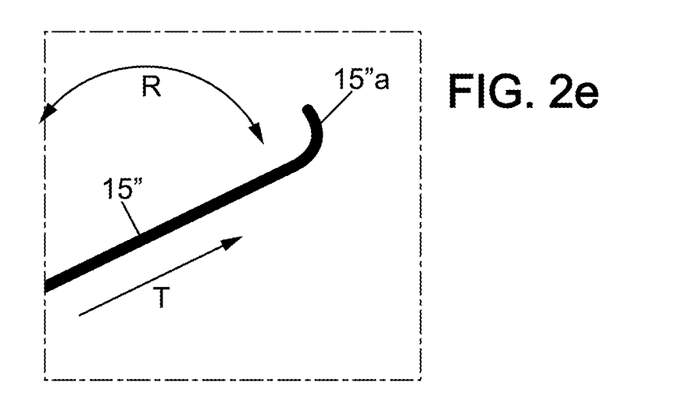
Figure 2F:
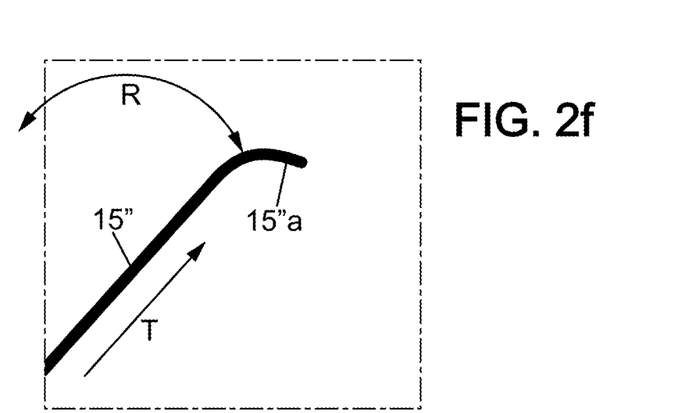

In connection with FIGS. 2d to 2f, the third mode of operation is going to be presented.

The catheter guide 15" and bent-back tip 15"a thereof progress in translation T along the guide 15", while, simultaneously, the catheter guide 15" and the bent-back tip 15"a thereof undergo an alternating rotation R around the axis of the catheter guide 15".

The three FIGS. 2d, 2e and 2f show the bent-back tip 15"a in various positions of angular orientation during the alternating rotation.

The translation speed T is relatively slow, whereas the frequency of alternating rotation R is relatively high. With this third mode of operation, having slow simultaneous slow translation with rapid alternating rotation, the catheter guide 15"a is able to easily pass by sensitive or difficult areas in the human circulatory system. This property of rapid rotation over a short range of translation is what allows the passage through the delicate area without hindrance and without risk of catching on the wall of the patient's blood vessel.

Figure 3:
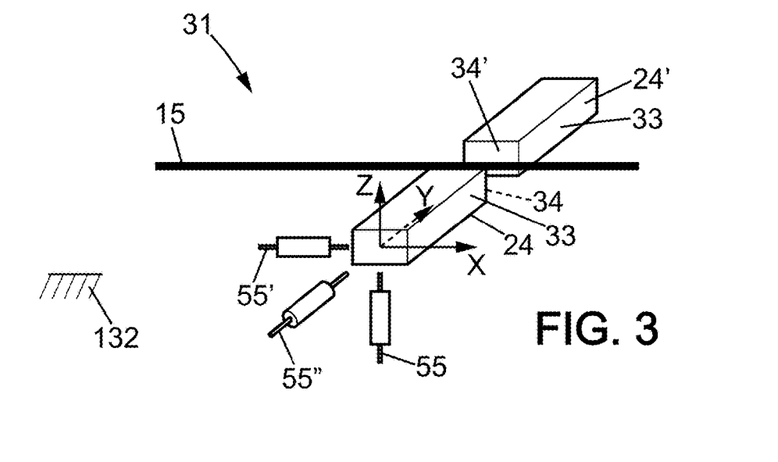
FIG. 3 is a perspective sketch of a portion of a drive module in released configuration.

FIG. 3 shows a drive module 131 according to a first embodiment. This drive module 131 is suited for driving along flexible medical member 15 extending along the longitudinal direction X. It will be noted that the longitudinal direction X near the drive module 131 is not strictly the same as that of the long flexible medical member 15 near its end but that a translation and/or a rotation of the long flexible medical member 15 along/around the longitudinal direction X near the drive module 131 will drive a translation and/or a rotation of the long flexible medical member 15 respectively along/around the longitudinal direction thereof near the end thereof.

The drive module 131 includes a base 132 and at least one drive member 24 mounted mobile relative to the base 132. The drive member 24 is, for example, mounted mobile relative to the base 132.

In the example shown, the drive module 131 further comprises a second drive member 24'. The drive member 24, also called hereafter first drive member, and the second drive member 24' together form a pair of drive members 33. The pair of drive members 33 comprises two drive members which together engage for generating a movement of the long flexible medical member 15 relative to the base 132. In the example shown, the second drive member 24' is mounted mobile relative to the base 132. The second drive member 24' is, for example, mounted mobile relative to the base 132.

The first drive member 24 and the second drive member 24' are paired for simultaneous movement. For example, the first and second drive members 24, 24' can be commanded individually, independently of each other, but according to synchronized respective commands. As a variant, a shared command can be provided which is distributed to one and the other of the first and second drive members 24, 24' by mechanical or electronic connection between their command systems.

Each drive member 24, 24' comprises a drive surface 34, 34' respectively. The long flexible medical member 15 is arranged between the drive surfaces 34, 34' of the drive members 24, 24' of a single pair. To set the ideas, the drive surfaces 34, 34' are separated from each other along the direction Y.

The pair of drive members 24, 24' can be placed in a released configuration, shown in FIG. 3, in which the drive surface 34, 34' of the drive members 24, 24' of the pair of drive members 33 is not engaged with the long flexible medical member 15.

The pair of drive members 33 can be placed in a drive configuration in which the drive surfaces 34, 34' of the drive members of the pair of drive members are engaged with the long flexible medical member 15 to be driven. The force applied by a drive member on the long flexible medical member in this configuration is for example of order a few Newtons (5-30 N for example). The restoring means, described above, are arranged for example to return the pair of drive members to released configuration, which provides a safety function, for example in case of outage of electric power.

To place the pair of drive members 33 alternately in released and drive configurations, a relative displacement of one towards the other of the two drive members 24, 24' can be ordered. This displacement can for example be the displacement of one drive member 24 relative to the base with the other remaining fixed. As a variant, the two drive members 24, 24' can both move towards each other relative to the base.

In the example, a displacement along the Y direction is intended.

In the embodiment shown, both drive members 24, 24' are mobile relative to the base along one degree of freedom. This degree of freedom is different from the one allowing the alternate placement of the drive members in the released and drive positions. It is in particular provided that the drive members 24, 24' are mobile relative to the base along one degree of freedom in their drive configuration. Thus, the displacement of the drive members along one degree of freedom in their drive configuration generates a displacement of the long flexible medical organ relative to the base 132.

An example will be described below in more detail in connection with FIGS. 4a to 4e. This example describes the generation of a movement in translation of the long flexible medical member along the longitudinal direction X thereof.

Figure 4A:
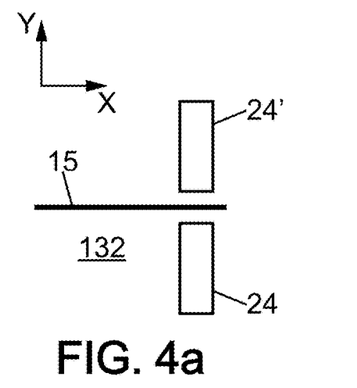
FIGS. 4a to 4e are simplified drawings showing a cycle of driving the catheter in translation according to an embodiment.
Figure 4B:
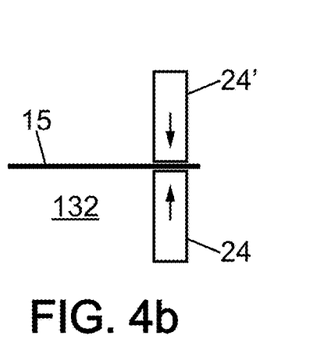

The starting position, shown in FIG. 4a, corresponds to that of FIG. 3 described above. In a first step, the released configuration shown in FIG. 4a changes to the drive configuration (FIG. 4b). According to the example, this change is done by a movement of the two drive members in opposing directions along the Y direction. The amplitude of this movement can depend on the long flexible medical member 15 to be driven. A guide, with a smaller diameter than the catheter, can require a larger amplitude movement from the same starting position than the catheter.

Figure 4C:
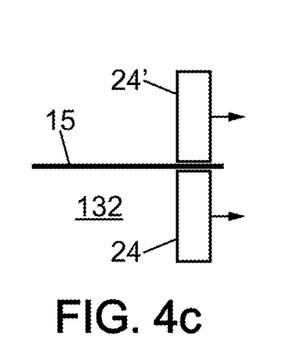

In drive configuration, a simultaneous displacement of the drive members in the same direction is generated along the longitudinal direction X according to a first direction, which generates an identical movement of the long flexible medical member 15 (FIG. 4c).

Figure 4D:
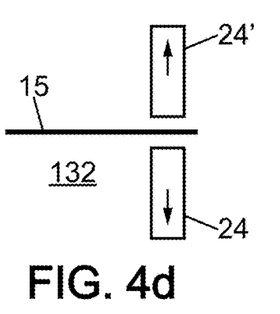

The drive configuration shown in FIG. 4c changes to the released configuration (FIG. 4d). According to the example, this change is done by a movement of the two drive members in opposite directions along the Y direction, in the direction of opposing the direction for changing the drive members from the drive configuration to the released configuration.

Figure 4E:
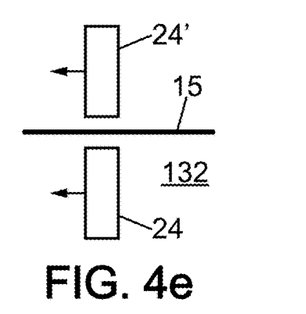

In released configuration, a simultaneous (or independent) displacement of the drive members in the same direction is generated along the longitudinal direction X according to a second direction opposite the first direction, which doesn't generate any movement of the long flexible medical member 15 (FIG. 4e). The initial configuration is thus restored.

The above steps can be repeated in a cyclically ordered manner for generating a translation of the long flexible medical member along a long course (for example of order several meters) along the longitudinal direction X in the first direction.

The displacement of the long flexible medical member along a long course along the longitudinal direction X in the second direction can be done by a series of operations opposite those which were just described.

The frequency of the cycle can be adjustable and commandable. In particular, a low-frequency can be provided for the insertion of the long flexible medical member in the patient, even several low-frequency levels, to allow in particular a slow navigation in difficult environments. A rapid frequency can be provided, for example for a withdrawal, even an emergency withdrawal. The displacement amplitudes for each cycle can also be adjustable.

For the translation, speeds included between 0.1 and 200 mm/s are conceivable.

An example will be described below in more detail in connection with FIGS. 5a to 5e. This example describes the generation of a movement in rotation of the long flexible medical member around the longitudinal direction X thereof.

Figure 5A:
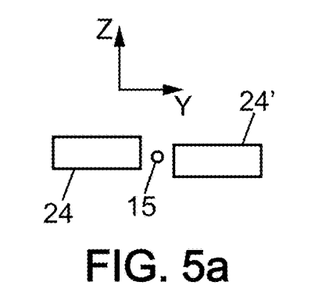
FIGS. 5a to 5e are simplified drawing showing a cycle of driving the catheter in rotation according to an embodiment.
Figure 5B:
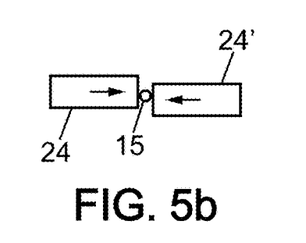

The starting position, shown in FIG. 5a, corresponds to that of FIG. 3 described above. In a first step, the released configuration shown in FIG. 5a changes to the drive configuration (FIG. 5b). According to the example, this change is done by a movement of the two drive members in opposing directions along the Y direction. This change is the same as what was already described in connection with FIGS. 4a, 4b above.

In drive configuration, a simultaneous displacement of the drive members in opposite direction is generated along a direction Z transverse to the longitudinal direction X, different from the direction Y, which generates a rotational movement of the long flexible member 15 (FIG. 5c) around the longitudinal direction X. In particular, the long flexible medical member rolls, preferably without sliding, on the drive surfaces 34, 34' of the drive member is 24, 24'. As a variant, only one of the two drive members can be moved, the other remaining fixed.

Figure 5C:
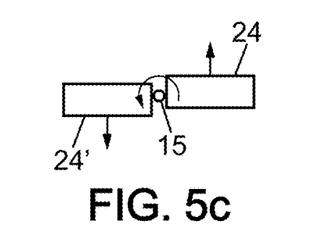
Figure 5D:
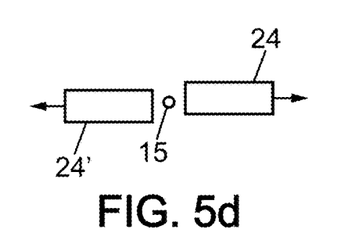

The drive configuration shown in FIG. 5c changes to the released configuration (FIG. 5d). According to the example, this change is done by a movement of the two drive members in opposing directions along the Y direction, in the direction of opposing the direction for changing the drive members from the drive configuration to the released configuration.

Figure 5E:
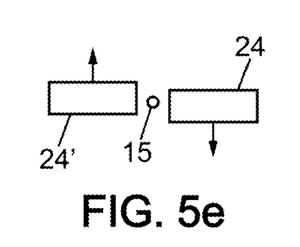

In released configuration, a simultaneous (or independent) displacement of the drive members is generated along the Z-direction, opposite the displacement described above in connection with FIG. 5c, which doesn't generate any movement of the long flexible medical member 15 (FIG. 5e). The initial configuration is thus restored.

The above steps can be repeated in a cyclically ordered manner for generating a rotation of the long flexible medical member along a long course (for example several times 360°) around the longitudinal direction X in a first direction of rotation.

The displacement of the long flexible medical member along a long course around the longitudinal direction X in the second direction of rotation opposite the first can be done by a series of operations opposite those which were just described.

In the description above, the degree of rotation of the free end of the flexible medical member inside the patient's body must be monitored by imaging. Just the same, as a variant or in addition, it is also possible to seek to verify upstream the amplitude of the rotation applied to the flexible medical member near the drive module. This is done with a knowledge of the diameter of the long flexible medical member near the drive members 24, 24'. In fact, the angle of rotation of the long flexible medical member for a given displacement of the actuating members depends on the ratio between the diameter of the long flexible medical member and the course of the drive members. This diameter can be predefined and stored in the command station 11. It is sufficient to inform the command station 11 in advance of the type of catheter used, the type in question comprising the diameter. As a variant, it is also possible to detect in situ the diameter of the long flexible medical member. If the released configuration of each drive member constitutes a reference position, the position of the drive member in drive configuration can be known, for example, by using an encoding system on the actuator associated with each drive member and serving to move the drive member from the released configuration thereof to the drive configuration thereof.

By knowing the position of both drive members in drive configuration, and by knowing the separation between the drive surfaces 34, 34' of both drive members in their released configuration, the spacing between the two drive surfaces in drive configuration can be determined and from that the diameter of the long flexible medical member can be determined.

This knowledge can also be used for detecting the end of a withdrawal movement of the long flexible medical member. In fact, if the command station 11 detects a sudden variation of the diameter detected over time during a command for withdrawal of the long flexible medical member, that most likely means that the long flexible medical member has been entirely withdrawn from the patient, and even from the module. The diameter detected then can be either zero or, for example, the diameter of the guide if the guide then extends between the two drive members.

The tightening on the long flexible medical member in drive configuration can also be managed.

In fact, in drive configuration, the current applied to the actuators is proportional to the tightening force applied to the long flexible medical member. It is therefore possible to determine the tightening applied to the catheter based on the measurement of this current. In practice, it is possible to provide near the command station 11 various current settings for the actuators, arranged in an acceptable range of tightening outside of which there can be a risk either of the long flexible medical member sliding out of grip, or of damaging the long flexible medical member with an excessive mechanical stress from the drive members.

The control of the tightening on the long flexible medical member can be done for any movement applied to the catheter, not just for the movement in rotation described above.

The determination of the diameter of the long flexible medical member could be done for other catheter displacement implementations than the repeated cyclical commands described here.

Thus, independently of the repeated cyclical commands described here, it seems that an embodiment of the invention relates to a robotic drive module for long flexible medical member comprising:

A base 132;
A pair 33 of drive members 24, 24' each having a drive surface 34, 34', where the pair 33 of drive members 24, 24' can be placed by at least one actuator 26 in a drive configuration in which the drive surfaces 34, 34' of the drive members 24, 24' of the pair 33 of drive members 24, 24' are engaged with the long flexible medical member to be driven and arranged on either side thereof;
The pair 33 of drive members 24, 24' is mounted mobile relative to the base 132 along a degree of freedom between a first and second position;
A command member 18, 11 suited for commanding a displacement from the first to the second position relative to the base 132 of the drive members 24, 24' of the pair 33 of drive members 24, 24' in drive configuration with a relative representative signal to the actuator 26 (for example in a repeated cyclic way), thereby driving the long flexible medical member relative to the base 132.

In particular, the relative representative signal to the actuator serves to determine a separation between the drive surfaces 34, 34', with the command member 18, 11 commanding a displacement determined from the separation relative to the base 132 of the drive members 24, 24' of the pair 33 of drive members 24, 24' thus driving a rotation of controlled amplitude of the long flexible medical member relative to the base 132.

In particular, the relative representative signal to the actuator serves to manage a tightening force applied on the long flexible medical member within an allowable range of tightening forces.

In the above two example embodiments, a sequenced displacement is described during which one waits for the completion of the displacement of one drive member along one direction before starting another displacement.

Just the same, given that the actuations of the drive members along various degrees of freedom can be made independent by using independently the three actuation systems 55, 55', 55" described above, the displacement of the drive member along two degrees of freedom can be implemented simultaneously. For example, the displacement of the drive members from the position in FIG. 5c to that in FIG. 5e could include an intermediate phase between a first phase of pure separation and a second phase of pure return to the initial position, where these two movements are combined. A similar intermediate phase is also conceivable between the position of FIG. 5d and the position of FIG. 5b between the phase of pure return to the initial position and the phase of pure approaching. By following this line, it is possible to no longer have pure phases of return to the initial position, pure separation or pure approaching, insofar as there is no risk of generating parasitic movements of the long flexible medical member.

Additionally, while FIGS. 4a-4e showed independently a movement of pure translation of the long flexible medical member and FIGS. 5a-5e showed a movement of pure rotation, these two movements could alternatively be combined. In engaged configuration, it would be sufficient to combine the movements of the drive members suited for generating simultaneously translation and rotation.

The preceding example includes a single pair of drive members.

As a variant, several pairs of drive members could be provided. For example, and for description, two pairs of drive members could be provided. The drive members 24", 24''' from the second pair 33' can be similar to those from the first pair, and in particular comprise drive surfaces 34", 34''' and be actuated from the remote command station 11, or else the local command box 18, according to an implementation similar to those for the first pair. The first pair 33 and the second pair 33' of drive members can be offset relative to each other along the longitudinal axis X of the long flexible medical member. According to a first example, the two pairs 33, 33' can be intended to be coplanar in their released configuration. Meaning that they can be provided relative to a base 132 shared by the two pairs. As a variant, the bases 132, 132' for each picture could be independent, even non-coplanar.

The actuations of the two pairs can be synchronized. For example, the actuators for the two pairs can generate simultaneous identical movements of the two pairs.

As a variant, the two pairs can be actuated in synchronization for generating movements offset in phase. Meaning that a first pair 33 can be in drive configuration while another pair is in released configuration, and vice versa. For example, there is always at least one pair in drive configuration. At any given moment, it can involve the first, second or even both pairs at the same time. The hold on the long flexible medical member can be improved with such a configuration. In particular, when the long flexible medical member is moved while rubbing against an anatomical area of the patient, it must be possible to provide a sufficient hold thereon for overcoming the local resistance to the displacement. This is even more difficult when the long flexible medical member is slippery, for example because it is kept in a solution.

Figure 6A:
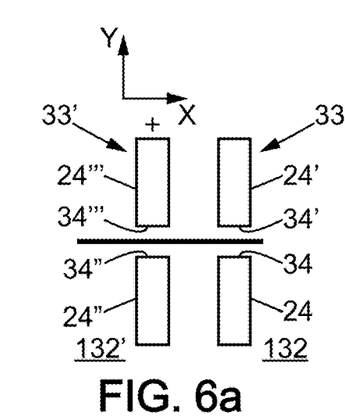
FIGS. 6a to 6f are simplified drawing showing a cycle of driving the catheter in translation according to an embodiment.
Figure 6B:
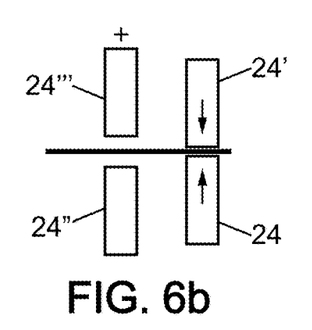
Figure 6C:
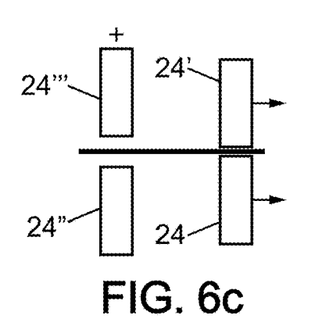
Figure 6D:
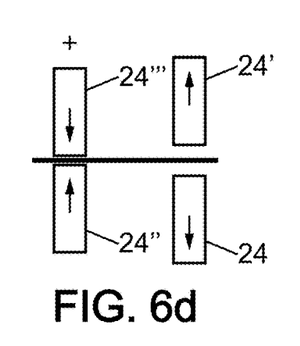
Figure 6E:
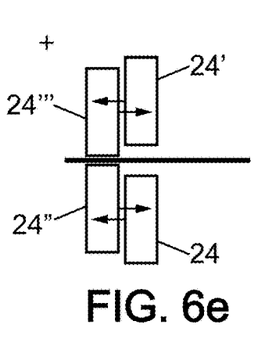
Figure 6F:
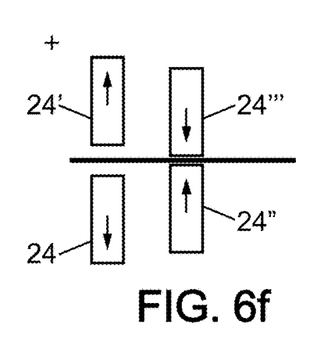

In FIGS. 6a to 6f an example is given for illustration of a mode of driving in translation. In these figures, a reference which is fixed over time is designated by the "+" sign. The movement of the first pair, represented in FIGS. 6a to 6e, was already described above in connection with FIGS. 4a to 4e. FIG. 6f shows the same position as FIG. 6b, the displacement being circular.

The FIGS. 6b to 6f show the displacements of the second pair 33' during one cycle. These displacements are out of phase relative to those of the first pair; the position shown in FIG. 6d for the second pair corresponds to the position from FIG. 6b for the first pair, and so on.

The two pairs are spaced so as to avoid any collision, in particular such as shown in FIG. 6e, where the second pair undergoes a displacement in the direction in which the long flexible medical member advances and where the first pair undergoes a displacement in the opposite direction.

For illustration, the FIG. 6a can represent an initial state in which the two pairs are located away from the long flexible medical member. During the startup of the system, the first pair will be commanded and then, out of phase, the second pair.

This implementation applies for other movements than translation. This implementation applies for more than two pairs. In this case, the pairs are, as applicable, all out of phase with each other, or some pairs can be in phase with each other.

The invention claimed is:

1. A robotic method of driving catheter or guide, or even catheter and guide, is provided for piloting an assembly of drive members and comprising:
A first mode of operation in which the assembly of drive members advances the guide and/or the catheter in translation;
A second mode of operation in which the assembly of drive members turns the guide and/or the catheter around itself;
wherein the method also comprises:
A third mode of operation in which the assembly of drive members simultaneously advances the guide and/or the catheter in translation and turns the guide and/or the catheter around itself alternately in one direction and then in the other direction,
wherein:
in the third mode of operation, the assembly of drive members simultaneously advances the guide and/or the catheter in translation (T) according to the variations of the command from a human machine interface and turns the guide and/or the catheter automatically around itself alternately in one direction and then in the other direction.

2. The robotic method of driving catheter or guide, or even catheter and guide, according to claim 1, wherein:
In the third mode of operation, the assembly of drive members simultaneously advances the guide and/or the catheter in translation (T) according to the variations of the command from a human machine interface and automatically turns the guide and/or the catheter around itself alternately in one direction and then in the other direction, where the frequency of alternating rotation is proportional to the speed of translation.

3. The robotic method of driving catheter or guide, or even catheter and guide, according to claim 1, wherein:
In the third mode of operation, the assembly of drive members simultaneously advances the guide and/or the catheter in translation (T) and turns the guide and/or the catheter around itself alternately in one direction and then in the other direction, where the ratio between the frequency of alternating rotation and the speed of translation is adjustable by the user of the method.

4. The robotic method of driving catheter or guide, or even catheter and guide, according to claim 1, wherein:
In the third mode of operation, the advance in translation (T) of the guide and/or catheter is slower than in the first mode of operation, whereas the alternating rotation of the guide and/or catheter around itself is faster than the rotation (R) of the guide and/or of catheter around itself in the second mode of operation.

5. The robotic method of driving catheter or guide, or even catheter and guide, according to claim 1, wherein:
The guide is a wire having a bent back tip, with the bent-back tip advancing along a direction parallel to the wire while turning around the axis of the wire in the third mode of operation.

6. The robotic method of driving catheter or guide, or even catheter and guide, according to claim 5, wherein:
The bent-back tip of the guide undergoes at least two changes of direction of rotation (R) in the time that it advances a distance corresponding to the length of the bent-back tip, preferably at least four changes of direction of rotation (R), still more preferably at least 10 changes of direction of rotation (R).

7. The robotic method of driving catheter or guide, or even catheter and guide, according to claim 1, wherein:
The guide and/or catheter undergoes at least two changes of direction of rotation (R) in the time that it advances a distance corresponding to a length of 5 mm, preferably at least four changes of direction of rotation (R), still more preferably at least 10 changes of direction of rotation (R).

8. The robotic method of driving catheter or guide, or even catheter and guide, according to claim 1, wherein:
In the third mode of operation, the frequency of changing direction of rotation (R) of the guide and/or catheter is at least 1 Hz, preferably at least 3 Hz, still more preferably at least 10 Hz.

9. The robotic method of driving catheter or guide, or even catheter and guide, according to claim 1, wherein:
In the third mode of operation, the speed of translation (T) of the guide and/or catheter is it most 10 mm/s, preferably at most 3 mm/s, still more preferably at most 1 mm/s.

10. The robotic method of driving catheter or guide, or even catheter and guide, according to claim 1, wherein:
The third mode is used for passing through some areas of branching in the human circulatory system.

11. The robotic method of driving catheter or guide, or even catheter and guide, according to claim 1, wherein:
The third mode is used for passing through some areas of lesions in the human circulatory system.

12. A robotic method of driving catheter or guide, or even catheter and guide, is provided for piloting an assembly of drive members and comprising:
A first mode of operation in which the assembly of drive members advances the guide and/or the catheter in translation (T) depending on variations of the command from a human machine interface;
A second mode of operation in which the assembly of drive members turns the guide and/or the catheter around itself depending on variations of the command from a human machine interface;
wherein the method also comprises:
A third mode of operation in which the assembly of drive members simultaneously advances the guide and/or the catheter in translation (T) and turns the guide and/or the catheter around itself alternately in one direction and then in the other direction, depending on variations of the command from a human machine interface.

13. A robotic method of driving catheter or guide, or even catheter and guide, is provided for piloting an assembly of drive members and comprising:
A first mode of operation in which the assembly of drive members automatically advances the guide and/or the catheter in translation (T);
A second mode of operation in which the assembly of drive members automatically turns the guide and/or the catheter around itself;
wherein the method also comprises:
A third mode of operation in which the assembly of drive members automatically and simultaneously advances the guide and/or the catheter in translation (T) and turns the guide and/or the catheter around itself alternately in one direction and then in the other direction.

14. A robotic method of driving catheter or guide, or even catheter and guide, is provided for piloting an assembly of drive members and comprising:
A first mode of operation in which the assembly of drive members advances the guide and/or the catheter in translation (T);
A second mode of operation in which the assembly of drive members turns the guide and/or the catheter around itself;
wherein the method also comprises:
A third mode of operation in which the assembly of drive members simultaneously both advances the guide and/or the catheter in translation (T) and also successively alternates turning the guide and/or catheter around itself always in a single direction followed by stopping this rotation.

15. The robotic method of driving catheter or guide, or even catheter and guide, according to claim 14, wherein:
In the third mode of operation, said rotation lasts a shorter time than said stopping.

16. The robotic method of driving catheter or guide, or even catheter and guide, according to claim 15, wherein:
In said third mode of operation, said rotation lasts between 0.05 s and 0.2 s, preferably about 0.1 s, said stopping lasts between 0.3 s and 1 s, preferably about 0.5 s, and said translation speed is included between 1 mm/s and 5 mm/s, preferably being about 3 mm/s.

17. A robotic module for driving catheter or guide, or even catheter and guide, comprising an assembly of drive members that are structured and arranged so as to be able to be piloted:
In a first mode of operation, so as to advance the guide and/or catheter in translation (T);
In a second mode of operation, so as to turn the guide and/or the catheter around itself;
wherein the assembly of drive members is also structured and arranged so as to be able to be piloted:
In a third mode of operation, so as to simultaneously advance the guide and/or the catheter in translation (T) while also turning it around itself alternately in one direction and then in the other.

18. The robotic module for driving catheter or guide, or even catheter and guide, according to claim 17, wherein:
In the third mode of operation, the assembly of drive members simultaneously advances the guide and/or the catheter in translation (T) according to the variations of the command from a human machine interface and automatically turns the guide and/or the catheter around itself alternately in one direction and then in the other direction, where the frequency of alternating rotation is proportional to the speed of translation.

19. The robotic module for driving catheter or guide, or even catheter and guide, according to claim 17, wherein the assembly of drive members comprises:
A base;
A pair of drive members each having a drive surface, where the pair of drive members can be placed alternately in a drive configuration in which the drive surface s of the drive members of the pair of drive members are engaged with the guide and/or catheter to be driven and arranged on either side thereof, and in a released configuration in which the drive surface of the drive members of the pair of drive members are not engaged with the guide and/or the catheter;
The pair of drive members is mounted mobile relative to the base along a degree of freedom between a first and second position;
A command member suited for cyclic repeatedly commanding a displacement relative to the base of the drive members of the pair of drive members in drive configuration from the first to the second position, in that way driving the guide and/or catheter relative to the base, and a displacement relative to the base of the drive members from the pair of drive members in released configuration from the second to the first position without driving the guide and/or the catheter relative to the base.

20. The robotic drive module according to claim 19, wherein the translation (T) of the drive members relative to the base along a direction (Z) transverse to the local longitudinal direction (X) of the guide and/or catheter and in opposite directions is adapted for allowing winding of the guide and/or catheter on drive surface s around the local longitudinal direction of the guide and/or catheter.

21. The robotic drive module according to claim 19, wherein the base is a first base, the pair of drive members is a first pair of drive members and the robotic module further comprises:
A second base;
A second pair of drive members each having a drive surface, where the second pair of drive members can be placed alternately in a drive configuration in which the drive surfaces of the drive members of the second pair of drive members are engaged with the guide and/or catheter to be driven and arranged on either side thereof, and in a released configuration in which the drive surface of the drive members of the second pair of drive members is not engaged with the guide and/or the catheter;
The second pair of drive members is mounted mobile relative to the base along a degree of freedom between a first and second position;
The command member is further suited for cyclic repeatedly commanding a displacement relative to the base of the drive members of the pair of drive members in drive configuration from the first to the second position, in that way driving the guide and/or catheter relative to the base, and a displacement relative to the base of the drive members from the pair of drive members in released configuration from the second to the first position without driving the guide and/or the catheter relative to the second base.

* * * * *